US00PP22463P3

(12) United States Plant Patent
Bornstein

(10) Patent No.: US PP22,463 P3
(45) Date of Patent: Jan. 17, 2012

(54) ***GYPSOPHILA* PLANT NAMED 'PEARL BLOSSOM'**

(50) Latin Name: ***Gypsophila paniculata* L.**
Varietal Denomination: Pearl Blossom

(76) Inventor: Menachem Bornstein, Holon (IL)

( * ) Notice: Subject to any disclaimer, the term of this patent is extended or adjusted under 35 U.S.C. 154(b) by 2 days.

(21) Appl. No.: 12/658,809

(22) Filed: Feb. 16, 2010

(65) Prior Publication Data

US 2011/0203023 P1 Aug. 18, 2011

(51) Int. Cl.
*A01H 5/00* (2006.01)

(52) U.S. Cl. ..... Plt./354
(58) Field of Classification Search ..... Plt./354
See application file for complete search history.

*Primary Examiner* — Kent L Bell
(74) *Attorney, Agent, or Firm* — Jondle & Associates, P.C.

(57) ABSTRACT

A new cultivar of *Gypsophila* named 'Pearl Blossom' particularly characterized by vigorous growth potency and uniform flowering; high yields, especially after pruning; low artificial light requirements; relatively late flowering (9 to 10 weeks during summer and 14 to 15 weeks during late autumn); long, heavy, and stable branches that are of high quality year-round, pinching increases the stem number to a range of 7 to 9 heavy stems and up to 15 stems of medium size and weight; has big, white flowers that are full and of uniformly good quality year-round without distortion or color change; is convenient to harvest and use in floral arrangements; has a long vase life; and has good tolerance to Powdery Mildew, is disclosed.

2 Drawing Sheets

Genus and species: *Gypsophila paniculata* L.
Variety denomination: 'Pearl Blossom'.

BACKGROUND OF THE NEW PLANT

The present invention comprises a new and distinct cultivar of *Gypsophila,* botanically known *Gypsophila paniculata* L., and hereinafter referred to by the cultivar name 'Pearl Blossom'. 'Pearl Blossom' was discovered as a seedling resulting from an open pollination in April 2007 in Moshav Amioz, Negev, Israel among a group of unnamed *Gypsophila paniculata* L. plants. A single plant selection was subsequently chosen for further evaluation and for asexual propagation.

The new cultivar was first propagated in September 2007 in Moshav Amioz, Negev, Israel and has been asexually reproduced repeatedly by vegetative cuttings in Moshav Amioz, Negev, Israel for two years (approximately 10 generations). 'Pearl Blossom' has been found to retain its distinctive characteristics through successive asexual vegetative cuttings.

Plant Breeder's Rights for this cultivar have been applied for in Israel on Aug. 21, 2008. 'Pearl Blossom' has not been made publicly available more than one year prior to the filing date of this application.

SUMMARY OF THE INVENTION

The following are the most outstanding and distinguishing characteristics of this new cultivar when grown under normal commercial practices in open field cultivation (soil) in Moshav Amioz, Negev, Israel.

1. Vigorous growth potency and uniform flowering;
2. Relatively late flowering, 9 to 10 weeks during summer, 14 to 15 weeks during late autumn;
3. High yield, especially after pruning;
4. Low artificial light requirements;
5. Branches are stable, long, heavy, and of high quality all year round;
6. Pinching increases the stem number to a range of 7 to 9 heavy stems, up to 15 stems of medium size and weight;

7. Big, white flowers that are full and of uniformly good quality all year round without distortion or color change;
8. Convenient to harvest and use in floral arrangements;
9. Long vase life; and
10. Good tolerance to Powdery Mildew.

DESCRIPTION OF THE PHOTOGRAPHS

This new *Gypsophila* plant is illustrated by the accompanying photographs. The colors shown are as true as can be reasonably obtained by conventional photographic procedures. The photographs are of a plant about 10 weeks old in August 2009 and grown from rooted cuttings in open field cultivation (soil) in Moshav Amioz, Negev, Israel under conditions which approximate those generally used in commercial practice.

DESCRIPTION OF THE NEW CULTIVAR

Figure 1:
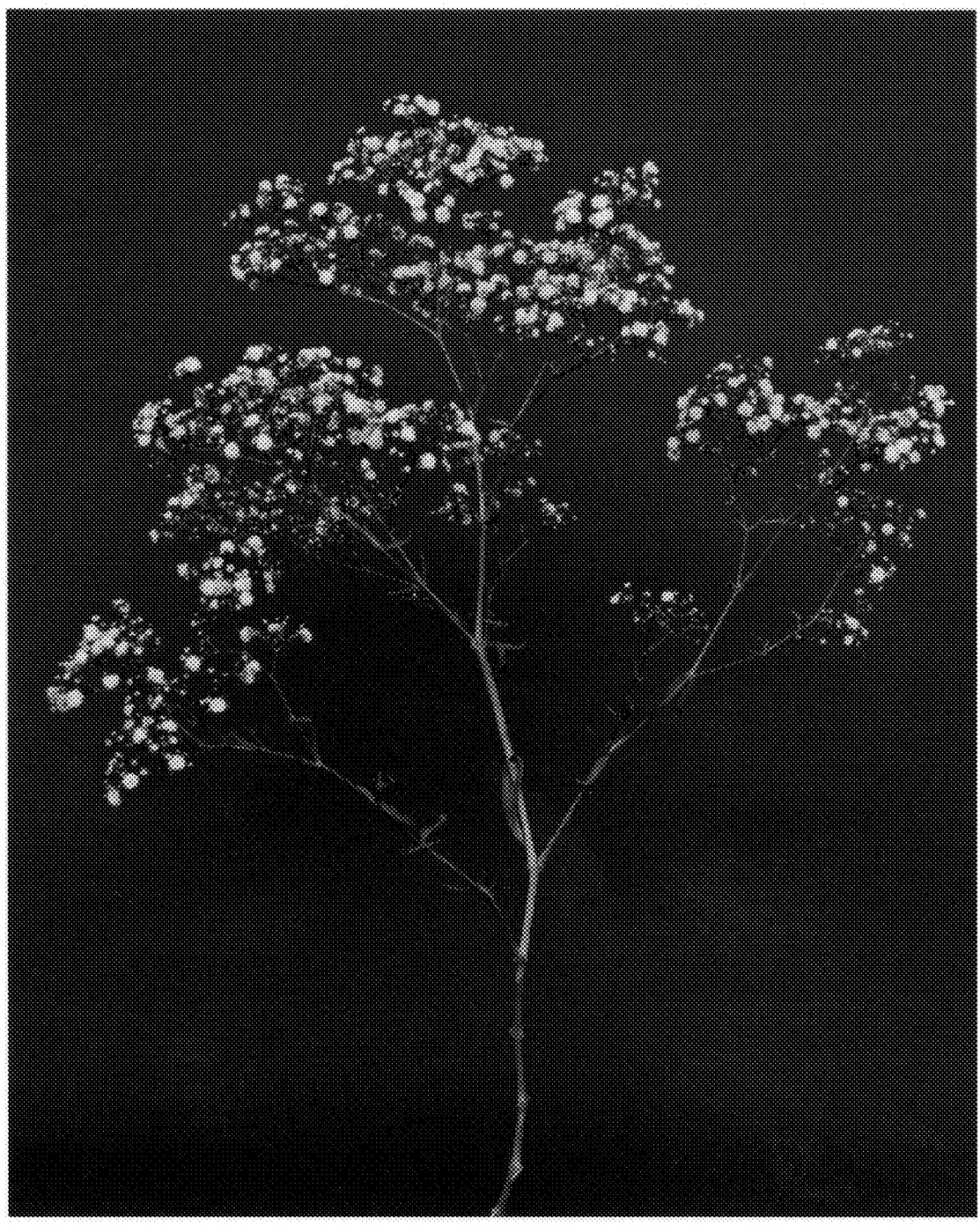
FIG. 1 shows a flowering stem.
Figure 2:
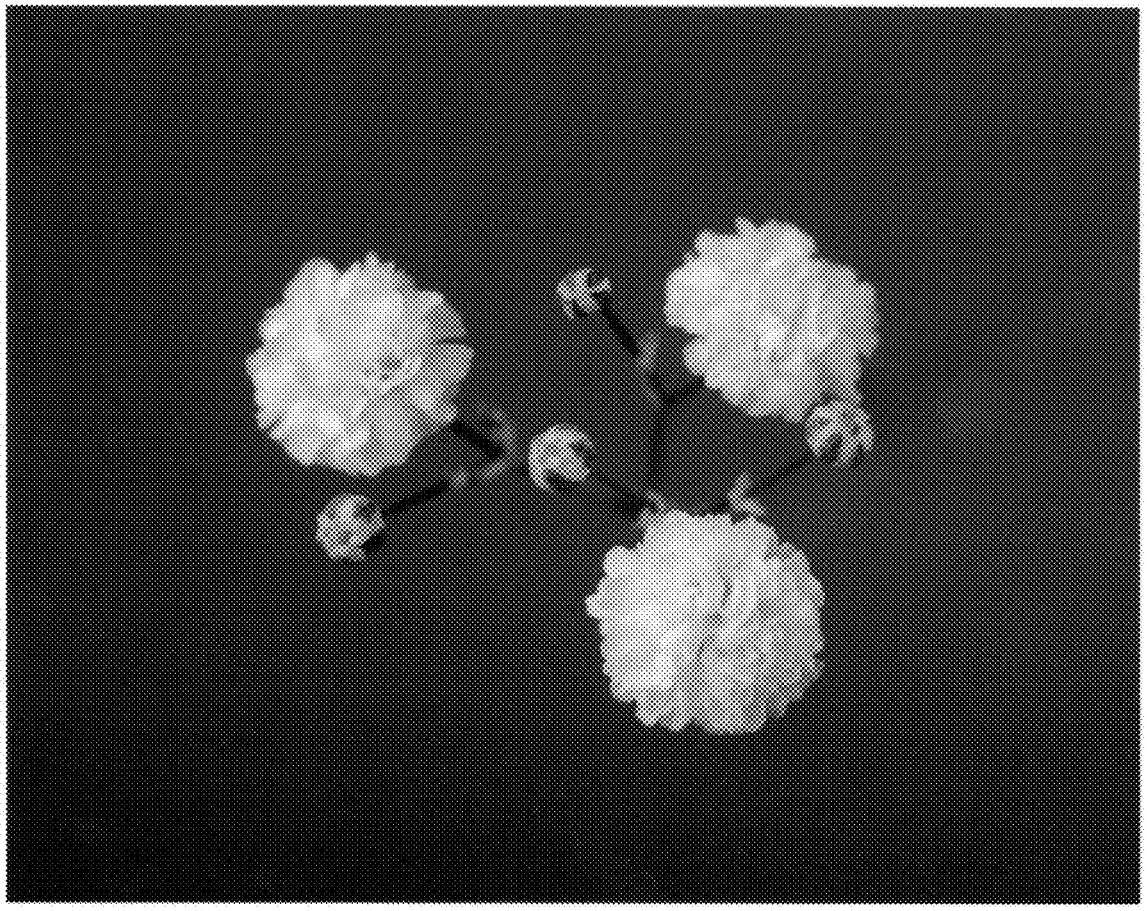
FIG. 2 shows a close up of the flowers and buds.

The following detailed descriptions set forth the distinctive characteristics of 'Pearl Blossom'. The data which define these characteristics were collected from asexual reproductions carried out in Moshav Amioz, Negev, Israel during the summer of 2009. The plant history was taken on 10 week-old plants in open field cultivation (soil) that were pinched once on June 30, 2009. The color readings were determined under natural light. Color references are to The R.H.S. Colour Chart of The Royal Horticultural Society of London (R.H.S.) (2001).

DESCRIPTION OF THE NEW PLANT

Classification:

*Genus and species.*—*Gypsophila paniculata* L.
*Common name.*—Baby's Breath.
*Variety name.*—'Pearl Blossom'.

Plant:
- *Form.*—Upright shrub type.
- *Habit.*—Perennial.
- *Plant height.*—100 cm.
- *Plant width (spread).*—60 cm.
- *Flowering habit.*—Year round in periodic flushes depending on growing conditions.
- *Time to produce a finished flowering plant.*—10 weeks from planting to flowering during the summer.
- *Propagation type.*—Vegetative cuttings.
- *Time to initiate roots.*—2 to 3 weeks.
- *Root description.*—Light brown, woody spike main root with branched fibrillary secondary roots.

Flowering stems:
- *Quantity per plant.*—7 to 9.
- *Color.*—RHS 147C (Yellow-Green).
- *General description.*—Panicle.
- *Stem strength.*—Stable.
- *Length.*—80 cm.
- *Diameter.*—50 cm.
- *Internode length.*—6 to 7 cm at upper part.
- *Texture.*—Glabrous.

Leaves:
- *Arrangement.*—Opposite.
- *Shape.*—Lanceolate.
- *Apex.*—Acute.
- *Base.*—Cuneate.
- *Margin.*—Entire.
- *Color, immature leaf.*—Upper surface: RHS 137A (Green). Lower surface: RHS 137B (Green).
- *Color, mature leaf.*—Upper surface: RHS 137A (Green). Lower surface: RHS 137B (Green).
- *Length.*—9.0 cm.
- *Width.*—1.5 cm.
- *Texture.*—Pubescent.
- *Venation pattern.*—Parallel.
- *Venation color.*—Upper surface: RHS 137A (Green). Lower surface: RHS 137B (Green).
- *Petiole.*—Absent.

Flowers:
- *Inflorescence type.*—Compound cymes with numerous double flowers, panicle shaped.
- *Flowering season.*—Year-round under 12 hours light and above.
- *Lastingness of individual flowers on the plant.*—10 to 12 days.
- *Lastingness of the flowers as a cut flower.*—10 to 12 days.
- *Flower width.*—0.9 cm.
- *Flower depth.*—0.6 cm.
- *Flower shape.*—Oblate and consisting of many petals.
- *Fragrance.*—Typical of *Gypsophila.*
- *Number of inflorescences per plant.*—7 to 9.
- *Number of flowers per inflorescence.*—400 to 600, dependent upon how the stem is cut.
- *Inflorescence.*—Length (height): 80 cm. Diameter: 50 cm.
- *Pedicel.*—Length: 0.5 cm. Diameter: 0.5 mm. Strength: Stable. Texture: Glabrous. Color: RHS 147C (Yellow-Green).

Peduncle:
- *Length.*—80 cm to 90 cm.
- *Diameter.*—0.7 cm at the basal end.
- *Texture.*—Glabrous.
- *Color.*—RHS 147C (Yellow-Green).

Flower buds:
- *Color.*—RHS 155A (White).
- *Shape.*—Oblate.
- *Length.*—0.3 cm.
- *Diameter.*—0.4 cm.

Petals:
- *Arrangement.*—Globular.
- *Quantity.*—40 to 50.
- *Shape.*—Spathulate.
- *Apex.*—Emarginated-wavy.
- *Base.*—Cuneate.
- *Margin.*—Entire.
- *Size.*—Length: 0.4 cm. Width: 0.2 cm.
- *Color.*—When opening and fully opened: Upper surface: RHS 155D (White). Lower surface: RHS 155D (White).
- *Surface texture (for both upper and lower surfaces).*—Smooth.

Sepals:
- *Arrangement.*—Cup-shaped.
- *Quantity.*—5 to 7.
- *Shape.*—Lanceolate.
- *Apex.*—Acute.
- *Base.*—Cuneate.
- *Margin.*—Entire.
- *Size.*—Length: 0.3 cm. Width: 0.1 cm.
- *Color, both upper and lower surfaces.*—RHS 147C (Yellow-Green).
- *Surface texture, both upper and lower surfaces.*—Pubescent.

Reproductive organs: None observed

Fruit and seed set: None observed

Disease and insect resistance: Typical of species, with a relative resistance to Powdery Mildew.

COMPARISON WITH COMMERCIAL CULTIVAR

'Pearl Blossom' differs from the commercial comparison variety 'Perfecta' (patent status unknown) in that 'Pearl Blossom' has low artificial light requirements and has a good tolerance to Powdery Mildew, while 'Perfecta' has high artificial light requirements and is sensitive to Powdery Mildew.

I claim:

1. A new and distinct cultivar of *Gypsophila* plant named 'Pearl Blossom' as shown and described herein.

* * * * *